United States Patent [19]

Buysch et al.

[11] Patent Number: 4,918,232

[45] Date of Patent: Apr. 17, 1990

[54] PROCESS FOR SEPARATING ANILINE DERIVATIVES

[75] Inventors: Hans-Josef Buysch, Krefeld; Michael Hüllmann, Heppenheim; Lothar Puppe, Burscheid, all of Fed. Rep. of Germany

[73] Assignee: Bayer Aktiengesellschaft, Leverkusen, Fed. Rep. of Germany

[21] Appl. No.: 213,069

[22] Filed: Jun. 29, 1988

[30] Foreign Application Priority Data

Jul. 21, 1987 [DE] Fed. Rep. of Germany ....... 3724018

[51] Int. Cl.$^4$ .............................................. C07C 85/26
[52] U.S. Cl. .................................................... 564/437
[58] Field of Search ................................ 564/437, 424

[56] References Cited

U.S. PATENT DOCUMENTS

| | | | |
|---|---|---|---|
| 4,467,126 | 8/1984 | Zinnen | 568/937 |
| 4,480,129 | 10/1984 | Priegnitz et al. | 564/424 |
| 4,633,018 | 12/1986 | Zinnen | 564/424 |

FOREIGN PATENT DOCUMENTS

| | | |
|---|---|---|
| 0007983 | 2/1980 | European Pat. Off. |
| 0151924 | 11/1979 | Japan |
| 128372 | 6/1919 | United Kingdom |
| 2031873 | 4/1980 | United Kingdom |

*Primary Examiner*—Richard L. Raymond
*Assistant Examiner*—Peter G. O'Sullivan
*Attorney, Agent, or Firm*—Sprung, Horn, Kramer & Woods

[57] ABSTRACT

A process for separating from each other aniline and aniline derivatives having different numbers of C atoms bound to the N atoms is disclosed herein, this process being characterized in that a mixture of the substances mentioned is treated in liquid phase with zeolites of the faujasite type at a temperature from 0° C. to 190° C.

19 Claims, No Drawings

PROCESS FOR SEPARATING ANILINE DERIVATIVES

BACKGROUND OF THE INVENTION

The present invention relates to a process for separating from each other aniline derivatives having a different number of C atoms bound to the N atom.

Aniline and N-alkylated aniline derivatives are of great importance in the synthesis of valuable intermediates. For example, N,N-dimethylaniline is an important starting material for the preparation of dyes of the triphenylmethane series (Michler's ketone, methyl violet, crystal violet and others). Monomethylaniline is, in addition to being used for the preparation of dyes, used mainly as an intermediate for pharmaceutical preparations.

The industrial synthesis of N-alkylated aniline derivatives from aniline and suitable alkylating agents generally gives mixtures of substances which are alkylated to different degrees and, in some cases, also still contain starting material. To separate the mixtures of compounds formed, complicated and expensive processes are necessary. For example, methylation of aniline in the presence of methanol gives a mixture of N-monomethylaniline and N,N-dimethylaniline and, in some cases, even aniline. Due to the small difference in boiling points of these liquids, a vacuum distillation achieves a satisfactory separation only at very high reflux ratios. If higher purities are required of the N-methylaniline, it must be, in addition, further treated with toluene sulphochloride or with phthalic anhydride (Ullmanns Enzyklopädie der technischen Chemie, (Ullmann's Encyclopaedia of Industrial Chemistry), 3rd edition, vol. 3 (1953), p. 652).

It was therefore desired to simplify those expensive and complicated separations.

SUMMARY OF THE INVENTION

Suprisingly, it has now been found that aniline and aniline derivatives having different numbers of C atoms bound to the N atom can be separated from each other very selectively by the means of faujasite zeolites.

DETAILED DESCRIPTION OF THE INVENTION

Such separations using crystalline solids are hardly known in the literature. Only in the case of toluidine isomers has the absorption by zeolite CaX been described in U.S. Pat. No. 3,069,470 where para-selectivity was found to a certain degree. U.S. Pat. No. 4,480,129 also describes a method for concentrating p-toluidine by means of X and Y zeolites modified with transition metals, which, however, involves also using complicated solvent mixtures which, in turn, are difficult to separate off. Despite these complicated stopgap measures, the separation factor is hardly improved. It could not be expected, given this prior art, that the separations which were carried out would exhibit the extraordinarily high selectivity according to the invention. The point is that, in contrast to the toluidines, in the case of N-alkylated aniline derivatives free rotation around the (alkyl)-C-N-bond and modification of the molecular configuration is possible, while the individual toluidine isomers have rigid molecular configurations of different shapes which makes it reasonable also to expect different adjustments to certain cavities in the zeolites and therefore more selective separations.

A process for separating from each other aniline and aniline derivatives having different numbers of C atoms bound to the N atoms has now been found, this process being characterized in that a mixture of the substances mentioned is treated in liquid phase with zeolites of the faujasite type.

As a rule, the separation according to the invention relates to a mixture consisting of two aniline derivatives. Even in a mixture consisting of three or more substances, the separation according to the invention has, however, such a high efficiency that it either meets the desired requirements or leads to simpler mixtures of substances which can be further separated according to the invention or by conventional methods.

In the mixture consisting of aniline and aniline derivatives to be separated, the substances to be separated have different numbers of C atoms bound to the N atom. Examples of such mixtures of substances are those in which different alkyl substituents are present on the N atom, such as a mixture consisting of N-methylaniline and N-ethylaniline or a mixture consisting of N-ethylaniline and N-butylaniline. Further examples of mixtures of substances are those which are alkylated to a different degree, for example a mixture consisting of aniline and N-methylaniline or a mixture consisting of N-ethylaniline and N,N-diethylaniline. A typical mixture of three substances would be represented, for example, by a mixture consisting of aniline, N-methylaniline and N,N-dimethylaniline.

The aniline derivatives to be separated according to the invention can be described by the following formula

in which

R[1], R[2] and R[3] independently of each other stand for hydrogen or $C_1$-$C_4$-alkyl and in which furthermore R[3] can also additionally denote fluorine, chlorine or bromine or $C_1$-$C_4$-alkoxy.

As defined by the process according to the invention, a minimum of two different substances covered by the formula (I) are in each case to be used for the separation. Covered by the formula (I) are, for example, the following compounds: aniline, N-methylaniline, N-ethylaniline, N-isopropylaniline, N-n-propylaniline, N-n-butylaniline, N-sec.-butylaniline, N-tert.-butylaniline, N,N-dimethylaniline, N,N-diethylaniline, N,N-di-n-propylaniline, N,N-di-isopropylaniline, N,N-di-n-butylaniline, N,N-di-sec.-butylaniline and also the corresponding ortho-, meta- or para-toluidine derivatives or the corresponding aniline derivatives which additionally have an ethyl, propyl or butyl group in ortho, meta or para position on the aromatic nucleus, the corresponding ortho-, meta- or para- chloro-, -bromo- or -fluoroaniline derivatives or o-, m-, p-methoxy-, ethoxyaniline derivatives.

Preferred forms of aniline derivatives which may be mentioned are those of the formula

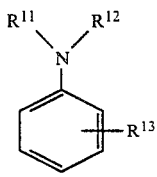

(II)

in which $R^{11}$, $R^{12}$ and $R^{13}$ independently of each other stand for hydrogen or $C_1$–$C_3$-alkyl.

Particularly preferred forms of aniline derivatives which may be mentioned are those of the formula

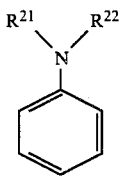

(III)

in which $R^{21}$ and $R^{22}$ independently of each other denote hydrogen, methyl or ethyl.

According to the invention, the aniline derivatives to be separated are present in liquid phase. As far as a mixture of such aniline derivatives to be separated represents a liquid at the selected reaction temperature, this liquid can be treated as such according to the invention. If the aniline derivatives to be separated are present as solids, they can be dissolved in a suitable inert solvent. Liquid aniline derivatives can also be diluted with such inert solvents.

Suitable inert solvents are aliphatic or aromatic hydrocarbons or haloaromatics. In the preferred method, those inert solvents are used which have a boiling point below 160° C. at atmospheric pressure. Examples of such solvents are n-pentane, n-hexane, n-heptane, isooctane, isodecane, isododecane, cyclohexane, methylcyclohexane, benzene, toluene, xylene, chlorobenzene or bromobenzene.

The process according to the invention is carried out by using zeolites of the faujasite type. Such faujasites occur in nature, but can also be prepared synthetically. In the preferred method, synthetic faujasites are used.

Faujasites for the process according to the invention can be described by the formula $$(1.0 \pm 0.2)Me_{2/n}O \cdot Al_2O_3 \cdot (2-6)SiO_2 \cdot ZH_2O$$

in which Me is one of the cations described further below n indicates the charge of the cation and Z is a number from 1–10.

Faujasites having an $SiO_2/Al_2O_3$ ratio of 2 to 3 are usually referred to as zeolite X, while those having an $SiO_2/Al_2O_3$ ratio of 3 to 6 are referred to as zeolite Y. The cation Me is exchangeable. Faujasites and cation exchange are known and, for example, described in detail in D. W. Breck, Zeolite Molecular Sieves, John Wiley & Sons, Inc., New York 1974.

The cations Me can be those of the groups Ia, IIa, IIb, IVa, IVb, VIa, VIIa or VIII, based on the short version of the periodic table. The cation can also be a proton $H^+$. In the preferred method, the faujasite contains cations of groups Ia, IIa, IVa or IVb or a proton $H^+$. In the particularly preferred method, the faujasite contains the cations of Na, K, Cs, Ca, Ti, Sn or a proton $H^+$.

The amount of faujasite used is 10 to 500% by weight, preferably 100 to 350% by weight, based on the amount of the aniline derivatives to be separated.

In addition to the surprisingly high separation capacity of the zeolites of the faujasite type within the process according to the invention, the particularly good efficiency of the alkali forms of the faujasites must be considered completely unexpected, for alkali zeolites are rated in the abovementioned U.S. Pat. No. 4,480,129 as virtually unusable.

The process according to the invention can be carried out in a conventional apparatus known to the person skilled in the art, for example conducting it batchwise in a stirring vessel or in a column apparatus for continuous operation. The shape and dimensions of these reaction apparatuses can, of course, be optimized.

The treatment according to the invention of the mixtures of aniline derivatives to be separated is carried out at a temperature of 0° C. to 190° C., preferably at 10° to 150° C., particularly preferably at 15° to 120° C. The pressure for the process according to the invention is not critical; in general, it is carried out at atmospheric pressure.

After the process according to the invention is completed, the liquid phase is drained off from the faujasite. It contains one part of the mixture of the aniline derivatives to be separated in a highly concentrated form. If an inert solvent was also used, it can be separated off by distillation. The inert solvent selected is one whose boiling point is sufficiently different from that of the concentrated part of the mixture.

Present on the faujasite is the remaining starting mixture of aniline and aniline derivatives to be separated, being concentrated in a reverse proportion to that of the part of the mixture which is present in the liquid phase. After draining the liquid phase, the faujasite is brought into contact with a polar liquid to regenerate it and to use it again for the process according to the invention. Through this regeneration, the other part of the mixture of aniline derivatives separated according to the invention is recovered.

Polar liquids for this process are for example aliphatic amines, alkanols, ethers, water or mixtures thereof. Further polar liquids which may be used in principle are known to the expert; however, he/she will select relatively low-boiling polar liquids which can be easily separated from the aniline and the aniline derivatives to be separated off from the faujasite and from the faujasite. Examples of such polar liquids are butylamine, diethylamine, dipropylamine, methanol, ethanol, diethyl ether, isopropanol, n-propanol, water and mixtures thereof. A low boiling point of such polar liquids also makes it possible to bring them into contact with the faujasite in vapour form. Therefore, after draining the liquid phase, the faujasite is regenerated with such a polar liquid or vapour thereof at a temperature of 10° to 200° C., preferably 40° to 150° C., particularly 60° to 120° C. If the polar liquid is to be used without significant evaporation at higher temperatures within the ranges mentioned, the process can also be carried out in a manner known to the expert under pressure, for example under the internal pressure of the system.

Polar liquids used are preferably lower alkanols and/or water, particularly preferably methanol, ethanol, water or mixtures thereof.

The advantages of the process according to the invention consist in the extraordinarily high selectivities, in the simple procedure for separating the aniline derivatives mentioned and in the low process temperatures required. For example, the treatment of the mixtures of aniline derivatives to be carried out continuously in column apparatuses and the likewise continuous regeneration of the faujasite yields an extraordinarily high output per apparatus unit.

The following examples illustrate the process according to the invention in more detail without limiting it to these examples.

EXAMPLE 1

A mixture of 2.42 g of N-ethylaniline (44.8% by weight of the total mixture) and 2.98 g of N,N-diethylaniline (55.2% by weight) was dissolved in cyclohexane, brought into contact with 16 g of powdered NaY zeolite and stirred at 25° C. for 60 minutes. The solution was subsequently filtered off from the zeolite and tested by gas chromatography. According to the analysis, the filtrate contains 4.2% of N-ethylaniline and 95.8% of N,N-diethylaniline. The same results are obtained by using isododecane or benzene as the solvent.

EXAMPLE 2

A mixture of 2.14 g of N-methylaniline (46.9% by weight of the total mixture) and 2.42 g of N,N-dimethylaniline (53.1% by weight) was dissolved in cyclohexane, brought into contact with 16 g of powdered SnY zeolite and stirred at 25° C. for 30 minutes. The analysis of the filtrate by gas chromatography showed a content of 15.9% by weight of N-methylaniline and 84.1% by weight of N,N-dimethylaniline.

EXAMPLE 3

A mixture of 1.86 g of aniline (43.5% by weight of the total mixture) and 2.42 g of N-ethylaniline (56.5% by weight) was dissolved in cyclohexane, brought into contact with 16 g of powdered NaX zeolite and stirred at 25° C. for 12 hours. The analysis of the filtrate by gas chromatography showed a content of 7.2% by weight of aniline and 92.8% by weight of N-ethylaniline.

EXAMPLE 4

A mixture of 1.86 g of aniline (46.5% by weight of the total mixture) and 2.14 g of N-methylaniline (53.5% by weight) was dissolved in cyclohexane, brought into contact with 16 g of powdered NaX zeolite at 25° C. and stirred for 30 minutes. The analysis of the filtrate by gas chromatography showed a content of 15.4% by weight of aniline and 84.6% by weight of N-methylaniline.

EXAMPLE 5

A mixture of 2.58 g of N-ethylaniline (47.8% by weight of the total mixture) and 2.82 g of N,N-diethylaniline (52.2% by weight) was dissolved in cyclohexane, brought into contact with 20 g of granular NaY zeolite (binder $SiO_2$) and stirred at 25° C. for 60 minutes under atmospheric pressure. The analysis of the filtrate by gas chromatography showed a content of 4.2% by weight of N-ethylaniline and 95.8% by weight of N,N-diethylaniline.

The mixture of aromatic amines trapped in the zeolite was subsequently desorbed in boiling methanol for 2 hours. Filtration and distilling of the methanol from the filtrate gave the amount of substances to be expected having a composition of 89% by weight of N-ethylaniline and 11% by weight of N,N-diethylaniline.

What is claimed is:

1. In a process comprising separating from each other aniline and aniline derivatives having a different number of C atoms bound to the N atoms, the improvement comprising treating a mixture of the substances mentioned in liquid phase with zeolites of the faujasite type at a temperature from 0° C. to 190° C.

2. A process according to claim 1, wherein synthetic faujasites of the type X or Y are used.

3. A process according to claim 1, wherein the faujasite contains one or more exchangeable cations of the groups Ia, IIa, IIb, IVa, IVb, VIa, VIIa or VIII of the periodic table in the short version or contains protons.

4. A process according to claim 3, wherein the faujasite contains cations of the groups Ia, IIa, IVa or IVb or contains protons.

5. A process according to claim 4, wherein the faujasite contains cations of Na, K, Cs, Ca, Ti, Sn or contains $H^+$.

6. A process according to claim 1, wherein the amount of faujasite is 10–500% by weight, based on the amount of aniline derivatives to be separated.

7. A process according to claim 6, wherein the amount of faujasite is 100–350% by weight, based on the amount of aniline derivatives.

8. A process according to claim 1, wherein the treatment is carried out at a temperature from 10° to 150° C.

9. A process according to claim 8, wherein the treatment is carried out at a temperature from 15° to 120° C.

10. A process according to claim 1, wherein after the treatment of the mixture of aniline derivatives and after the removal of the liquid phase the faujasite is regenerated with a polar liquid.

11. A process according to claim 10, wherein the polar liquid used is selected from the group consisting of aliphatic amines, alkanols, ethers, water and mixtures thereof.

12. A process according to claim 11, wherein the polar liquid used is a lower alkanol or water or a mixture thereof.

13. A process according to claim 10, characterized in that the regeneration is carried out at a temperature from 10° to 200° C.

14. A process according to claim 13, characterized in that the regeneration is carried out at a temperature from 40° to 150° C.

15. A process according to claim 14, characterized in that the regeneration is carried out at a temperature from 60° to 120° C.

16. A process according to claim 1, characterized in that the aniline derivate mixtures to be separated are those of formula

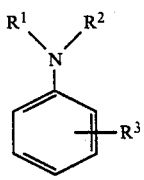

in which $R^1$, $R^2$ and $R^3$ independently of each other stand for hydrogen or $C_1$–$C_4$-alkyl and in which furthermore $R^3$ can also additionally denote fluorine, chlorine or bromine or $C_1$–$C_4$-alkoxy.

17. A process according to claim 16, characterized in that the mixtures to be separated consist of aniline derivatives which differ in the number of C atoms of $R^1$ or of $R^1$ and $R^2$.

18. A process according to claim 16, characterized in that the mixtures to be separated consist of aniline derivatives which differ in the degree of N-alkylation.

19. A process according to claim 1, characterized in that the mixture of the aniline derivatives is dissolved or diluted with the aid of an inert solvent.

* * * * *

UNITED STATES PATENT AND TRADEMARK OFFICE
CERTIFICATE OF CORRECTION

PATENT NO. : 4,918,232

DATED : April 17, 1990

INVENTOR(S) : Buysch et al.

It is certified that error appears in the above-identified patent and that said Letters Patent is hereby corrected as shown below:

| | |
|---|---|
| Col. 6, claim 13 lines 1-2 | Delete " characterized in that " and substitute -- wherein -- |
| Col. 6, claim 14 lines 1-2 | Delete " characterized in that " and substitute -- wherein -- |
| Col. 6, claim 15 lines 1-2 | Delete " characterized in that " and substitute -- wherein -- |
| Col. 6, claim 16 lines 1-2 | Delete " characterized in that " and substitute -- wherein -- |
| Col. 7, claim 17 lines 1-2 | Delete " characterized in that " and substitute -- wherein -- |
| Col's 7-8 claim 18 lines 1-2 | Delete " characterized in that " and substitute -- wherein -- |
| Col. 8, claim 19 lines 1-2 | Delete " characterized in that " and substitute -- wherein -- |

Signed and Sealed this

Fourteenth Day of January, 1992

Attest:

HARRY F. MANBECK, JR.

Attesting Officer

Commissioner of Patents and Trademarks